United States Patent [19]

Snoke et al.

[11] Patent Number: 5,624,397
[45] Date of Patent: Apr. 29, 1997

[54] CATHETER HAVING A MULTIPLE DUROMETER

[76] Inventors: Phillip J. Snoke, 2785 Arden Rd. NW., Atlanta, Ga. 30327; David S. Rowley, 4581-J Valley Pkwy., Smyrna, Ga. 30082; David G. Lincoln, 2860 Parkwood Rd., Smyra, Ga. 30080; Kirk W. Charles, 1725 Blossom Ln., Austell, Ga. 30001

[21] Appl. No.: 308,142

[22] Filed: Sep. 19, 1994

Related U.S. Application Data

[63] Continuation of Ser. No. 970,490, Nov. 2, 1992, Pat. No. 5,399,164.

[51] Int. Cl.$^6$ .................................................. A61M 37/00
[52] U.S. Cl. ................................................ 604/95; 604/282
[58] Field of Search .................. 604/95, 264, 280–282; 128/656–658, 772

[56] References Cited

U.S. PATENT DOCUMENTS

| | | |
|---|---|---|
| 922,985 | 5/1909 | Wappler. |
| 3,470,876 | 10/1969 | Barchilon. |
| 3,625,200 | 12/1971 | Muller. |
| 3,892,228 | 7/1975 | Mitsui. |
| 3,948,251 | 4/1976 | Hosono. |
| 4,273,111 | 6/1981 | Tsukaya. |
| 4,279,245 | 7/1981 | Takagi et al.. |
| 4,327,723 | 5/1982 | Frankhouser. |
| 4,390,012 | 6/1983 | Mizumoto. |
| 4,417,886 | 11/1983 | Frankhouser et al.. |
| 4,483,326 | 11/1984 | Yamaka et al.. |
| 4,515,592 | 5/1985 | Frankhouser. |
| 4,543,090 | 9/1985 | McCoy. |
| 4,577,621 | 3/1986 | Patel. |
| 4,580,551 | 4/1986 | Siegmund et al.. |
| 4,587,972 | 5/1986 | Morantte, Jr.. |
| 4,625,713 | 12/1986 | Hiraoka. |
| 4,644,960 | 2/1987 | Johans. |
| 4,745,908 | 5/1988 | Wardle. |
| 4,748,969 | 6/1988 | Wardle. |
| 4,753,222 | 6/1988 | Morishita. |
| 4,758,222 | 7/1988 | McCoy. |
| 4,793,326 | 12/1988 | Shishido. |
| 4,815,450 | 3/1989 | Patel. |
| 4,834,710 | 5/1989 | Fleck. |
| 4,844,053 | 7/1989 | Dittrich. |
| 4,890,602 | 1/1990 | Hake. |
| 4,893,613 | 1/1990 | Hake. |
| 4,906,230 | 3/1990 | Maloney et al.. |
| 4,911,148 | 3/1990 | Sosnowski et al.. |
| 4,986,258 | 1/1991 | Cho et al.. |
| 5,004,456 | 4/1991 | Botterbusch et al.. |
| 5,058,568 | 10/1991 | Irion et al.. |
| 5,125,906 | 6/1992 | Fleck. |
| 5,199,950 | 4/1993 | Schmitt et al.. |

FOREIGN PATENT DOCUMENTS

| | | |
|---|---|---|
| 0489937 | 7/1990 | European Pat. Off.. |
| WO91/01772 | 2/1991 | WIPO. |

*Primary Examiner*—John D. Yasko
*Attorney, Agent, or Firm*—Allen, Dyer, Doppelt, Milbrath & Gilchrist, P.A.

[57] ABSTRACT

The catheter is formed by a housing having a size and shape which fits readily into the hand of the user. An elongate tube is connected to and extends from the housing. The elongate tube is formed from a flexible polymeric material and constructed of three portions, a proximal portion, a medial portion, and a distal portion. Each of the portions is coaxial with one another and the longitudinal axis of the catheter housing. In addition, each of the portions has substantially the same outer circumference. The proximal and distal portions are formed of a flexible polymeric material which has a higher durometer of hardness than that of the medial portion. A pair of control wires extend longitudinally through the proximal, medial, and distal portions and parallel to the axis of the coaxial portions for selectively bending the portions in response to movement of the control wires. A control wheel is carried by the housing for controlling the movement of the control wires to thereby bend the selected portions and remotely manipulate the catheter within a human body. At least one lumen extends from the catheter body through each of the proximal, medial and distal portions of the elongate tube to form a working channel therein.

35 Claims, 2 Drawing Sheets

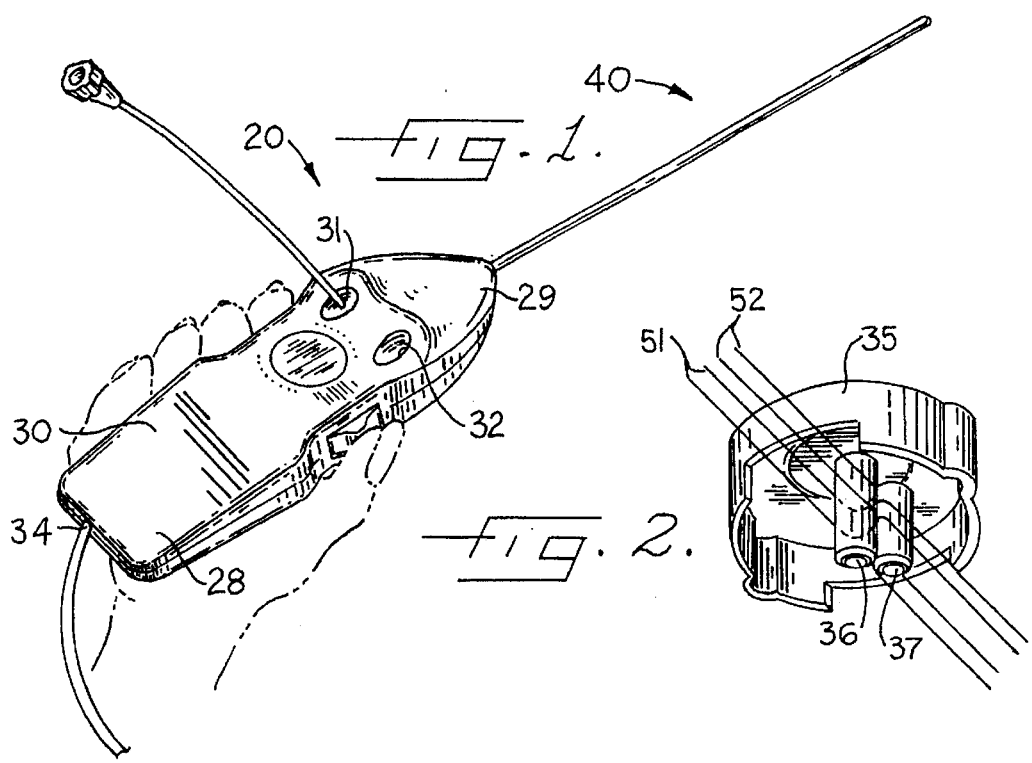
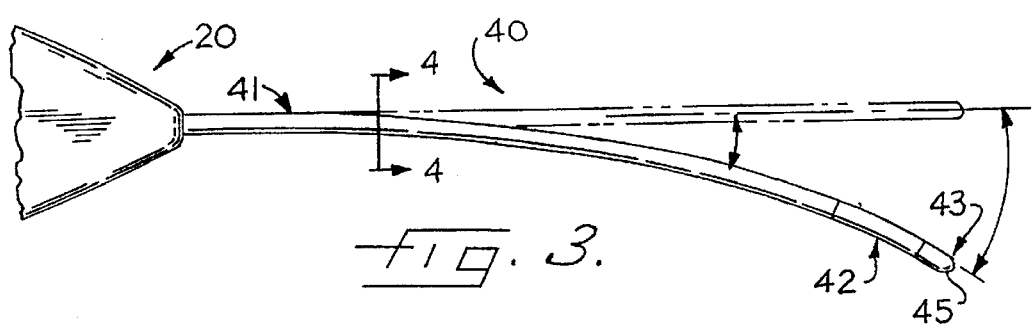
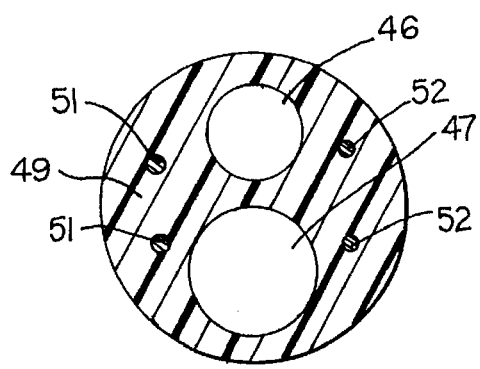
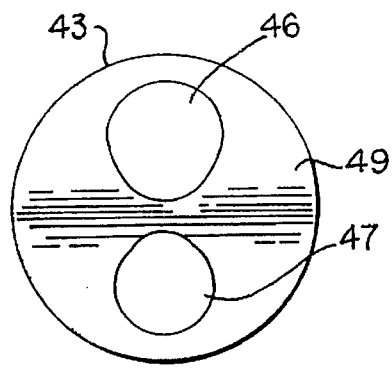

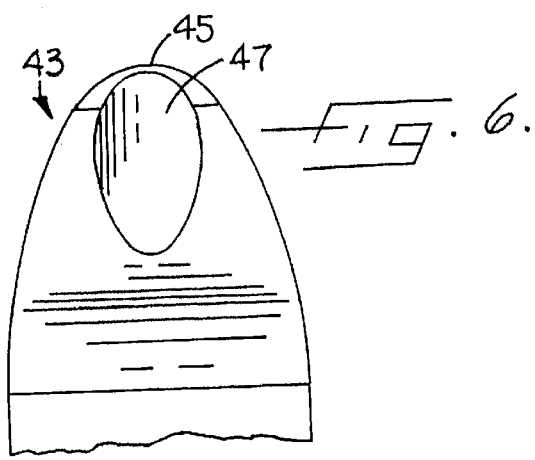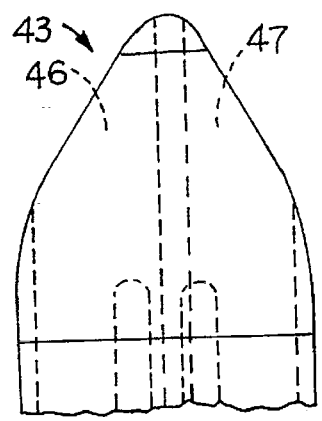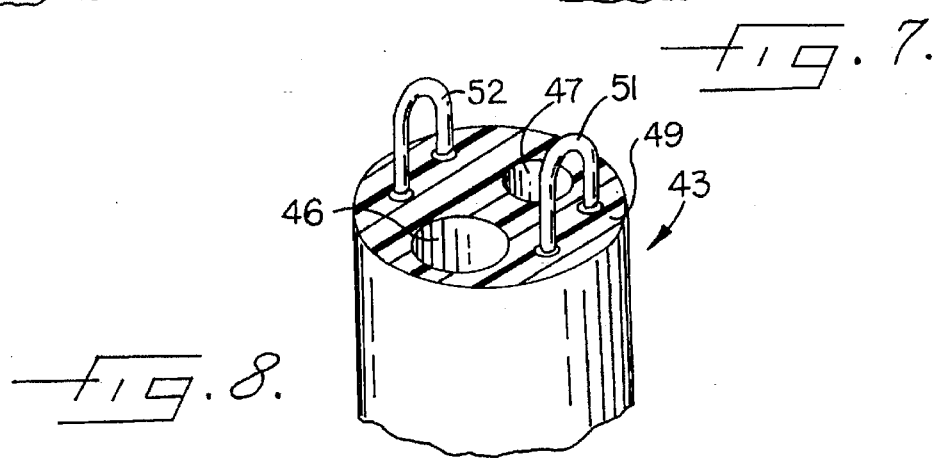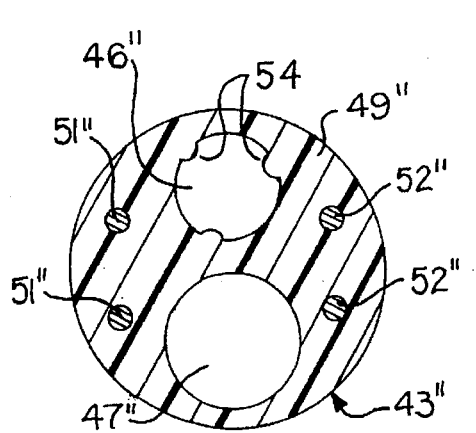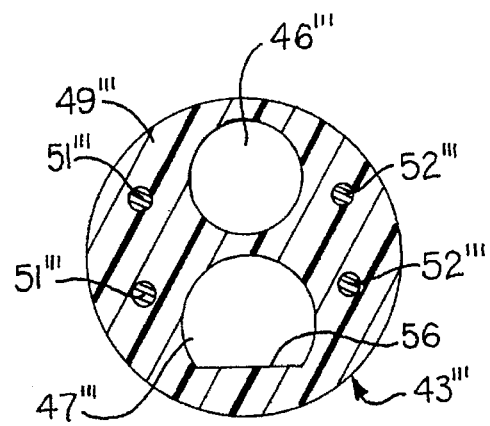

CATHETER HAVING A MULTIPLE DUROMETER

RELATED APPLICATIONS

This application is a continuation-in-part of U.S. patent application Ser. No. 07/970,490 filed Nov. 2, 1992 now U.S. Pat. No. 5,399,164 and is related to U.S. patent application Ser. No. 07/963,431 filed Oct. 19, 1992, now U.S. Pat. No. 5,423,311, Ser. No. 08/129,331 filed Sep. 30, 1993, now U.S. Pat. No. 5,354,266, Ser. No. 08/279,500 filed Jul. 22, 1994 and Issued U. S. Pat. No. 5,437,636 filed on Jul. 6, 1992, formerly U.S. patent application Ser. No. 07/908,403.

FIELD OF THE INVENTION

This invention relates to medical catheters, and more particularly to a steerable catheter for inserting into body vessels, cavities or tissue.

BACKGROUND OF THE INVENTION

Endoscopes and catheters are currently being used in a number of different medical procedures. For example, catheters are frequently used to introduce surgical tools, fluids, and other materials, such as radiographic contrast materials, angioplasty balloons, fiberoptic scopes, laser lights, and cutting instruments, into body vessels, cavities or tissue. In addition, catheters may also be used to perform therapeutic treatments by inserting surgical instruments or fluid through a treatment or working channel of an endoscope or catheter.

As the number of uses being made of catheters increases, the need to control and manipulate the catheter becomes more important. Various techniques and systems have been developed for guiding or steering the catheters into the body vessels or cavities for use of these tools, fluids, and other materials. Several catheters have been developed which rely on the use of wiring systems or linked segments within the catheter for controlling movement in a portion thereof. Examples of these devices may be seen in U.S. Pat. No. 3,948,251 by Hosono entitled "Flexible Tube Endoscope"; U.S. Pat. No. 4,279,245 by Takagi et al. entitled "Flexible Tube"; U.S. Pat. No. 5,058,568 by Irion, et al. entitled "Flexible Endoscope"; U.S. Pat. No. 4,844,053 by Dittrich entitled "Flexible Tubular Device"; U.S. Pat. No. 4,753,222 by Morishita entitled "Endoscopic Flexible Tube"; U.S. Pat. No. 4,580,551 by Siegmund, et al. entitled "Flexible Plastic Tube for Endoscopes And The Like"; and, U.S. Pat. No. 4,911,148 by Sosnowski, et al. entitled "Deflectable-End Endoscope With Detachable Flexible Shaft Assembly".

Other catheters have been developed which require the insertion of an instrument into a channel or lumen of the catheter to control the movement thereof. Examples of such devices may be seen in U.S. Pat. No. 922,985 by Wappler entitled "Endoscope"; U.S. Pat. No. 4,390,012 by Mizumoto entitled "Rigid Type Endoscope"; U.S. Pat. No. 4,577,621 by Patel entitled "Endoscope Having Novel Proximate and Distal Portions"; U.S. Pat. No. 4,587,972 entitled "Device For Diagnostic And Therapeutic Intravascular Intervention"; U.S. Pat. No. 4,625,713 by Hiraoka entitled "Instrument Incorporated In A Resectoscope"; U.S. Pat. No. 4,745,908 by Wardle entitled "Inspection Instrument With Flexible Shaft Having Deflection Compensation Means"; U.S. Pat. No. 4,748,969 by Wardle entitled "Multi-Lumen Core Deflecting Endoscope"; and U.S. Pat. No. 4,793,326 by Shishido entitled "Endoscope Having Insertion End Guide Means". These devices, although illustrating various control techniques, do not provide ease of insertion and control to the hand of the physician.

Other catheter control techniques may be seen in U.S. Pat. No. 3,892,228 by Mitsui entitled "Apparatus For Adjusting The Flexing Of The Bending Section Of An Endoscope"; U.S. Pat. No. 4,483,326 by Yamaka, et al. entitled "Curvature Control Mechanism In Endoscopes"; U.S. Pat. No. 4,543,090 by McCoy entitled "Steerable and Aimable Catheter"; U.S. Pat. No. 4,815,450 by Patel entitled "Endoscope Having Variable Flexibility"; U.S. Pat. No. 4,890,602 by Hake entitled "Endoscope Construction with Means For Controlling Rigidity and Curvature of Flexible Endoscope Tube"; U.S. Pat. No. 4,906,230 by Maloney, et al. entitled "Steerable Catheter Tip"; and, U.S. Pat. No. 4,893,613 by Hake entitled "Endoscope Construction With Means For Controlling Rigidity And Curvature Of Flexible Endoscope Tube". These control systems attempt to control portions of the catheter by inserting instruments therein or inserting wires or other control mechanisms within a tube of the catheter. Like the other known devices, however, the mechanisms for controlling these catheters are often awkward and bulky making both insertion and control of the catheter difficult.

Thus, there still exists a need to provide a catheter that allows for easy insertion into the body vessel, cavity or tissue and which provides for easy control and manipulation of the catheter by the physician to improve the simultaneous use of surgical tools, such as fiberoptic scopes or the like, and/or fluids needed for medical operations. Easy insertion and manipulation of the catheter increases the physician's ability to readily locate, isolate, view, and/or perform a surgical procedure at the desired area within the body vessel, cavity or tissue.

SUMMARY OF THE INVENTION

In view of the foregoing background, it is therefore an object of the present invention to provide a catheter that can be more easily inserted into a vessel, cavity or tissue of the human body and to provide improved control and flexibility for the user.

These and other objects, features, and advantages of the present invention are obtained by providing a catheter which has a housing of such a size and shape so as to be readily and comfortably held in the hand of the user. An elongate tube formed from three distinct portions preferably extends from and is connected to the housing. It is beneficial for the elongate tube to have a distal portion be coaxial with a medial portion and the medial portion be adjacent to and coaxial with a proximal portion. Preferably, the three portions are formed from a flexible polymeric material to ensure the resiliency of the elongate tube while having sufficient stiffness to maintain a substantially straight axis in the absence of an external force being applied thereto. It is advantageous for the distal portion to have substantially the same flexibility as the proximal portion, and have the medial portion be more flexible than the distal and proximal portions. The outer circumference of the tube is preferably substantially the same to ensure that the elongate tube easily inserts into the desired body cavity, vessel or tissue and that fluids, surgical instruments and other materials pass easily through lumens formed in the elongate tube of the catheter. The distal portion preferably converges to form a tip for easy access into and through a body vessel, cavity or tissue.

To decrease the amount of deformity of the elongate tube as it passes through ligaments or other tough tissue, it is desirable to have the distal portion of the elongate tube have a higher durometer of hardness, and as a result be relatively less flexible than the medial portion. Stated differently, it is beneficial for the medial portion of the elongate tube to have a lower durometer of hardness, and as a result have greater flexibility than both the proximal portion and the distal portion. This increased flexibility of the medial portion allows the distal portion of the elongate tube to bend about the medial portion through an angle of greater than 90°.

The catheter preferably includes a plurality of lumens which extend parallel to the axis of and extend through the proximal, medial, and distal portions to provide a working channel for receiving surgical tools and other materials therethrough to perform various treatments. Splines may be provided in the lumens for directing fluid around the distal portion to allow for cleaning of the surgical tool or other objects inserted therein.

To control and manipulate the elongate tube, it is beneficial to use control wires which preferably extend longitudinally through the proximal, medial, and distal portions and parallel to the axis of these portions for bending the elongate tube in response to movement of the control wires. It is advantageous to have a control wheel be carried by the housing for controlling the movement of the control wires to thereby bend the desired portions of the elongate tube and remotely manipulate the catheter within a human body.

The increased durometer of hardness of the distal portion results in a septum wall located between the lumens thereof being more resistant to tearing from the control wires which control movement of the elongate tube. This also has a secondary benefit of making the lumens of the elongate tube in the distal portion less likely to be damaged by instruments and other materials passing therethrough.

The distal portion of the elongate tube can preferably be moved relative to the longitudinal axis of the catheter to improve its ability to be controlled and manipulated inside the body. In addition, it is beneficial to be able to change the angular attitude of the proximal portion relative to the longitudinal axis without changing the angular attitude of the distal portion for purposes of manipulating the medial portion of the elongate tube.

BRIEF DESCRIPTION OF THE DRAWINGS

Some of the objects and advantages of the present invention having been stated, others will become apparent as the description proceeds when taken in conjunction with the accompanying drawings, in which:

FIG. 1 is a perspective view of the catheter having a multiple durometer hardness according to the present invention;

FIG. 2 is an enlarged view of the control wheel and control wires of the catheter according to the present invention;

FIG. 3 is a top plan view of a portion of the catheter illustrating the movement of the proximal, medial and distal portions of the elongate tube in response to movement of the control wheel;

FIG. 4 is an enlarged cross-sectional view taken along line 4—4 of FIG. 3 illustrating the working lumens and the control wires, as well as illustrating the similar outer circumference of the elongate tube of the catheter;

FIG. 5 is an enlarged end view of the catheter from the distal portion;

FIG. 6 is an enlarged side plan view of the distal portion of the catheter;

FIG. 7 is an enlarged side plan view of a distal portion of a catheter having dashed lines for indicating the working lumens and the wires within the distal portion;

FIG. 8 is an enlarged cut away view of distal portion illustrating the insertion of the control wires within the catheter;

FIG. 9 is an enlarged cross-sectional view similar to that shown in FIG. 4 illustrating another embodiment of the elongate tube of the catheter having splines located in one of the working lumens, permitting even flow of fluid around the distal end; and FIG. 10 is an enlarged cross-sectional view similar to that shown in FIG. 4 illustrating another embodiment of the elongate tube of the catheter having one working lumen include a flat portion to prevent unwanted rotation of an instrument located therein during a procedure.

DESCRIPTION OF A PREFERRED EMBODIMENT

The present invention now will be described more fully hereinafter with reference to the accompanying drawings in which a preferred embodiment of the invention is shown. This invention may, however, be embodied in different forms and should not be construed as limited to the embodiments set forth herein. Rather, the illustrative embodiments are provided so that this disclosure will be thorough and complete, and will fully convey the scope of the invention to those skilled in the art to which it pertains. Like numbers refer to like elements throughout.

Referring now to the drawings, FIG. 1 is a perspective view of the catheter generally designated at 20. The catheter 20 has a housing 30 which has a size and shape intended to readily conform to the hand of a user, enabling the catheter to be comfortably held during a medical procedure. The shape and structure of the housing 30 is described in detail in copending U.S. patent application Ser. Nos. 07/908,403 and 08/279,500 which are hereby incorporated herein by reference. The catheter 20 has an elongate tube 40 which is connected to the housing 30 and extends outwardly from an end 29 thereof. As shown best in FIG. 1, the housing 30 has access ports 31 and 32 for permitting access to a pair of working lumens 46 and 47 shown in FIG. 4. An access port 34, located within opposite end 28 of the housing 30, provides access to one of the lumens 46 or 47 for a fiberscope or the like. The structure of each of the access ports 31, 32, and 34 is disclosed in copending U.S. Pat. application Ser. No. 07/980,403.

FIGS. 3–5, illustrate, in greater detail, the elongate tube 40 of this embodiment. The elongate tube 40 is formed from a proximal portion 41, a medial portion 42 and a distal portion 43. Each of the portions is formed from a flexible polymeric material having sufficient stiffness to maintain the elongate tube 40 along a substantially straight axis in the absence of an external force being applied thereto. The elongate tube 40 of this embodiment is formed by extruding a polymeric material, preferably a thermoplastic such as polyurethane, but other polymeric materials, apparent to those skilled in the art, may also be used. The flexibility of each of the portions 41, 42, and 43, depends on the hardness characteristics of the polymeric material used to form the various portions of the elongate tube 40. The three portions of this embodiment have different durometer of hardness because the polyurethane material used in the extruding process has different durometer characteristics. The durometer characteristics are controlled to ensure that the desired variations in hardness and flexibility between each of the three portions 41, 42, and 43 is obtained. The durometer of hardness is directly related to the flexibility of the particular portion of the elongate tube 40. For instance, a high durometer of hardness will equate to a limited amount of flexibility whereas a low durometer of hardness is indicative of increased flexibility. In this particular instance, the proximal portion has a hardness durometer range between 75–85D, the medial portion between 45–55D, and the distal portion between 75–85D. It is to be understood that if desired, it is possible to manufacture at least the distal portion 43 of the elongate tube 40 of a hard plastic to increase the durometer of hardness.

The proximal 40, medial 42, and distal 43 portions are extruded so that they have substantially the same outer circumference throughout the elongate tube 40. The extrusions are then cut to the desired length of each of the three portions. As best seen in FIG. 3, the length of each portion of the elongate tube 40 decreases as it progresses from the proximal portion 41, to the medial portion 42, and the distal portion 43. Specifically, in this embodiment, the proximal portion 41 is approximately 4" in length, the medial portion 42 is approximately ¾" in length, and the distal portion 43 is approximately ⅛" in length. It is to be understood, however, that other proportions are possible for each of these portions of the elongate tube 40 and still remain within the spirit of the invention.

The three portions are then joined using adhesive, sonic welding, or radio frequency ("RF") welding. Preferably, RF welding is used to form the proximal, medial and distal portions into the single integral elongate tube 40. As a consequence, the distal portion 43 of the elongate tube 40 is more resistant to the external forces which might otherwise cause the tip or distal end of the elongate tube to become detached from the remainder of the elongate tube during use. Other joining techniques, such as solvent bonding, apparent to those skilled in the art, may also be used.

The lumens 46 and 47 are kept in line during the formation process by a mandrel of the proper size to ensure proper alignment. In addition, molding or other tube forming techniques, as well as the extruding discussed herein, may be used to form the various tube portions 41, 42 and 43. If the tube portions are molded, various hardening techniques, apparent to those skilled in the art, may also be used to form the varying flexibility of the tube portions.

As shown in FIG. 8, and as described in copending U.S. patent application Ser. Nos. 07/908,403 and 08/279,500, control wires 51 and 52 are inserted into the wire channels formed in the various portions 41, 42 and 43 and looped through the distal portion 43. The wires 51 and 52 are held under tension as the distal portion 43 is inserted into a tipping die. The die is heated and shaped to form a convergent tip 45 and then cooled. The looping of the wires 51 and 52 through the wire channels in the distal portion 43 not only secures the wires to a portion of the elongate tube 40 but also reduces the slippage of the wires as the wires 51 and 52 are moved longitudinally with respect to one another to bend the various portions 41, 42 and 43 of the elongate tube 40.

Movement of these flexible portions of the elongate tube 40 is controlled by a control means shown in FIG. 2 as a control wheel 35. The control wheel such 35 has stem portions 36, 37 which are connected to and enable the housing 30 to carry the control wheel such as in the manner disclosed in U.S. patent application Ser. Nos. 07/908,403 and 08/279,500. As shown in FIGS. 2 and 8, control wires 50 and 52 are attached to a portion of the housing 30, cross over and wrap around the stem portions 36 and 37, and form loops adjacent tip 45 in the distal portion 43. As a result, rotation of the control wheel 35 causes the control wires 51 and 52 to move within the elongate tube 40, which allows the user to selectively bend and thereby remotely manipulate various portions of the elongate tube of a catheter 20. It will be apparent that various other attaching or engaging locations may also be used, such as attaching the wires 51 and 52 to the control wheel 35 in some manner. Further, the control wires may also only extend into various portions 41, 42, or 43 of the elongate tube 40 for changing the angular attitude of the medial 42 or proximal 41 portions from the substantially straight axis separately from any changes in the angular attitude of the distal portion to thereby manipulate the medial 42 or the proximal portion. FIG. 3 illustrates the controlled movement of the catheter 20 in response to movement of the control wheel 35.

FIGS. 4 and 5 illustrate the location of the working lumens 46 and 47, which extend parallel to the longitudinal axis of the housing 30, the proximal 41, medial 42 and distal 43 portions, and the control wires 50 and 52 within the elongate tube 40. In the embodiment shown, the lumens 46 and 47 are oriented in vertical alignment above one another, internal to the control wires, and the lumens have a generally circular configuration. It is to be understood however, that the lumens need not have this orientation relative to each other and/or the control wires. Skilled artisan will recognize various other alternatives which are available while remaining within the spirit of this invention. Two alternative configurations of the lumens 46 and 47 are discussed in detail below.

FIGS. 5–8 illustrate views of the distal portion 43 of the catheter 20 and the construction thereof. FIG. 5 is an end view of the distal portion 43 of the catheter 20 illustrating the working lumens 46 and 47 which provide an access for a fiberoptic scope or the like into a vessel or cavity of the human body. FIG. 6 is a side plan view of the housing 30, showing one of the lumens 47 at the tip 45 of the distal end 43. The lumen 47 allows the medical tools, fluid, and other materials or objects to pass through the catheter 20 and into the target area of the human body. FIG. 7 is another side plan view of the housing 30, showing in phantom the location of the lumens 46 and 47.

FIG. 9 illustrates an alternative embodiment of the present invention where splines 54 are formed into at least one and possibly both of the lumens 46" and 47". The splines 54 operate to keep a medical instrument or tool centered within the lumen (in this embodiment 46") and away from the sides thereof, which allows fluid to evenly flow through the lumen and around the end of the instrument or tool for irrigation and/or cleaning thereof during a medical procedure.

FIG. 10 shows another embodiment of the lumen 47''' which has one flat surface 56 to limit or prevent any unwanted rotation of a medical tool or instrument, placed in lumen 47''' during a procedure.

Many modifications and other embodiments of the invention will come to mind in one skilled in the art to which this invention pertains having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed:

1. A catheter for easily inserting into a vessel, cavity or tissue of the human body to thereby provide improved flexibility and manipulation of a portion of the catheter within the vessel, cavity or tissue, said catheter comprising:

a housing configured to be readily held in the hand of a user;

a tubular proximal portion connected to and extending outwardly from said housing, said proximal portion formed of a flexible polymeric material;

a tubular medial portion coaxial with and integrally formed as a unitary piece with said proximal portion, said medial portion being formed of a flexible polymeric material and being more flexible than said proximal portion;

a tubular distal portion coaxial with and integrally formed as a unitary piece with said medial portion, said distal portion formed of a flexible polymeric material and being less flexible than said medial portion; and means responsive to a user of the catheter for controlling movement of at least said distal portion for manipulating said catheter within a human body.

2. A catheter according to claim 1, wherein said proximal, medial, and distal portions comprise substantially the same outer circumference.

3. A catheter according to claim 2, further comprising a pair of lumens extending parallel to the axis of said coaxial proximal, medial, and distal portions, for providing a working channel therein.

4. A catheter according to claim 3 further comprising a septum wall separating said lumens.

5. A catheter according to claim 4 wherein said distal portion comprises a thermoplastic material resistant to tearing of said septum wall, resistant to deformation of said distal portion when passing through tissue, and resistant to damage from medical instruments inserted therein.

6. A catheter according to claim 3 wherein at least one of said lumens comprises a plurality of splines for directing fluid around said distal portion for cleaning a medical instrument inserted therein.

7. A catheter according to claim 3 wherein one of said lumens comprises a flat surface therein for preventing unwanted rotation of a medical instrument inserted therein.

8. A catheter according to claim 3, wherein said pair of lumens extend into said housing for accessing said lumens therefrom.

9. A catheter according to claim 1, wherein said control means comprises:

a pair of control wires extending longitudinally through said proximal, medial, and distal portions and parallel to the axis of said coaxial portions for bending and thereby manipulating said flexible portions when said control wires are moved longitudinally with respect to one another; and a rotatable control wheel located within said housing, for engaging a portion of each of said control wires, so that rotation of said control wheel moves said wires and thereby changes an angular attitude of said elongate tube.

10. A catheter according to claim 9, wherein each of said control wires extends longitudinally from said proximal portion, through said medial portion, and into said distal portion, looped within said distal portion and extending longitudinally from said distal portion, through said medial portion, and into said proximal portion to thereby reduce slippage of said control wires as said wires are moved longitudinally with respect to one another.

11. A catheter according to claim 1 wherein said proximal portion, said medial portion, and said distal portion are welded together at ends thereof into an integral unit to form said elongate tube.

12. A catheter for easily inserting into a vessel, cavity or tissue of the human body to thereby provide improved flexibility and manipulation of a portion of the catheter within the vessel, cavity or tissue, said catheter comprising:

an elongate tube formed of a material having sufficient stiffness to maintain said elongate tube along a substantially straight axis in the absence of an external force applied thereto, said elongate tube having a distal portion, a medial portion and a proximal portion, each of said portions having substantially the same outer circumference, being integrally formed of a unitary piece of material, and said medial portion of said elongate tube being more flexible than said distal portion.

13. A catheter according to claim 12, wherein said proximal portion and distal portion have substantially the same flexibility.

14. A catheter according to claim 12, wherein said distal portion of said elongate tube further comprises a tip for ease of access into and through a body vessel, cavity, skin, or tissue.

15. A catheter according to claim 12, further comprising a wire extending longitudinally through said elongate tube for controlling a change in the angular attitude of said distal portion from said substantially straight axis to thereby remotely manipulate said distal portion of said catheter.

16. A catheter according to claim 12, further comprising a housing configured so as to be readily held in the hand of a user and connected to said proximal portion of said elongate tube to thereby provide control and manipulation thereof.

17. A catheter according to claim 12, wherein said material forming said elongate tube comprises a polymeric material.

18. A catheter according to claim 13, wherein said distal portion of said elongate tube comprises a pair of lumens extending parallel to the axis of said coaxial proximal, medial, and distal portions, for providing a working channel therein.

19. A catheter according to claim 18 further comprising a septum wall separating said lumens.

20. A catheter according to claim 19 wherein said distal portion comprises a thermoplastic material resistant to tearing of said septum wall, resistant to deformation of said distal portion when passing through tissue, and resistant to damage of said working channel from medical instruments inserted therein.

21. A catheter according to claim 21 wherein one of said lumens comprises a plurality of splines for directing fluid around said distal portion for cleaning a medical instrument inserted therein.

22. A catheter according to claim 21 wherein one of said lumens comprises a flat surface therein for preventing unwanted rotation of a medical instrument inserted therein.

23. A catheter for easily inserting into a vessel, cavity or tissue of the human body to thereby provide improved flexibility and manipulation of a portion of the catheter within the vessel, cavity or tissue, said catheter comprising:

a tubular proximal portion formed of a flexible polymeric material;

a tubular medial portion coaxial with and connected to and integrally formed as a unitary piece of material with a distal end of said proximal portion, said medial portion formed of a flexible polymeric material and having substantially the same outer circumference as said proximal portion, and said medial portion being more flexible than said proximal portion; and a tubular distal portion coaxial with connected to and integrally formed as a unitary piece of material with a distal end of said medial portion, said distal portion formed of a flexible polymeric material having substantially the same outer circumference as said medial portion and said proximal portion, and said distal portion having less flexibility than said medial portion.

24. A catheter according to claim 23, wherein said proximal, medial, and distal portions are formed from a single type of polymeric material.

25. A catheter according to claim 24, wherein said flexible polymeric material is a thermoplastic polymer.

26. A catheter according to claim 24, wherein said flexible polymeric material is polyurethane.

27. A catheter according to claim 23, wherein said proximal, medial, and distal portions are separate pieces joined into an integral unit to form said elongate tube.

28. A catheter according to claim 27 wherein said proximal, medial, and distal portions are joined by welding together said proximal, medial, and distal portions at respective common ends thereof.

29. A catheter according to claim 23, further comprising a pair of lumens extending parallel to the axis of said coaxial proximal, medial, and distal portions providing a working channel therein.

30. A catheter according to claim 29 further comprising a septum wall separating said lumens.

31. A catheter according to claim 30 wherein said distal portion comprises a thermoplastic material resistant to deformation when passing through tissue, resistant to tearing of said system wall, and resistant to damage of said working channel from medical instruments inserted therein.

32. A catheter according to claim 29 wherein one of said lumens comprises a plurality of splines for directing fluid around said distal portion for cleaning a medical instrument inserted therein.

33. A catheter according to claim 29 wherein one of said lumens comprises a flat surface therein for preventing unwanted rotation of a medical instrument inserted therein.

34. A catheter according to claim 29, further comprising a pair of control wires extending longitudinally through said proximal, medial, and distal portions and parallel to the axis of said coaxial portions for bending and thereby manipulating said flexible portions when said control wires are moved longitudinally with respect to one another.

35. A catheter according to claim 34, wherein each of said control wires extends longitudinally from said proximal portion, through said medial portion, and into said distal portion, looped within said distal portion and extending longitudinally from said distal portion, through said medial portion, and into said proximal portion to thereby reduce slippage of said control wires as said wires are moved longitudinally with respect to one another.

* * * * *